United States Patent [19]

Sutter et al.

[11] Patent Number: 4,484,570
[45] Date of Patent: Nov. 27, 1984

[54] DEVICE COMPRISING AN IMPLANT AND SCREWS FOR FASTENING SAID IMPLANT TO A BONE, AND A DEVICE FOR CONNECTING TWO SEPARATED PIECES OF BONE

[75] Inventors: Franz Sutter, Niederdorf; Fritz Straumann, Waldenburg; Joram Raveh, Oberbottigen, all of Switzerland

[73] Assignee: Synthes Ltd., Wayne, Pa.

[21] Appl. No.: 266,352

[22] Filed: May 22, 1981

[30] Foreign Application Priority Data

May 28, 1980 [CH] Switzerland ............... 4155/80

[51] Int. Cl.³ .................................................. A61F 5/04
[52] U.S. Cl. .................. 128/92 D; 128/92 B; 128/92 R
[58] Field of Search ........... 128/92 R, 92 A, 92 B, 128/92 BB, 92 BC, 92 D; 411/71, 72, 44, 393, 395

[56] References Cited

U.S. PATENT DOCUMENTS

| 2,267,925 | 12/1941 | Johnston ................. 128/92 BB |
| 2,699,774 | 1/1955 | Livingston ............... 128/92 BB |
| 3,255,747 | 6/1969 | Cochran et al. .......... 128/92 R |
| 4,332,036 | 6/1982 | Sutter et al. ............ 128/92 A |

FOREIGN PATENT DOCUMENTS

| 57925 | 8/1940 | Denmark ................. 411/71 |
| 586126 | 10/1933 | Fed. Rep. of Germany ........ 411/72 |
| 7226376 | 2/1974 | France . |
| 526985 | 5/1955 | Italy ....................... 411/71 |
| 566767 | 6/1923 | Switzerland . |
| 106842 | 1/1925 | Switzerland . |
| 569202 | 12/1973 | Switzerland . |
| 584855 | 12/1977 | U.S.S.R. .............. 128/92 B |
| 197804 | 4/1978 | U.S.S.R. .............. 128/92 B |

OTHER PUBLICATIONS

Clinical Articles, "New Concepts in Reconstruction of Mandibular Defects Following Tumor Resection", Raveh, Stich, Sutter and R. Greiner.

Primary Examiner—Richard J. Apley
Assistant Examiner—David J. Isabella
Attorney, Agent, or Firm—Davis, Hoxie, Faithfull & Hapgood

[57] ABSTRACT

A plate is provided with clearance holes and fastening screws. Each screw is provided in the region of its head with a clamping part subdivided into tongues by means of slots and provided with an internal opening bounded by a conical surface. To each screw belongs an expander having a conical outer surface. The expander is axially displaceable in relation to the clamping part to force the tongues of the clamping part apart and lock the screw in relation to the plate. A rigid connection between the plate and the screws is thus provided, even if reabsorption of bone material takes place at the bearing surface of the plate.

15 Claims, 19 Drawing Figures

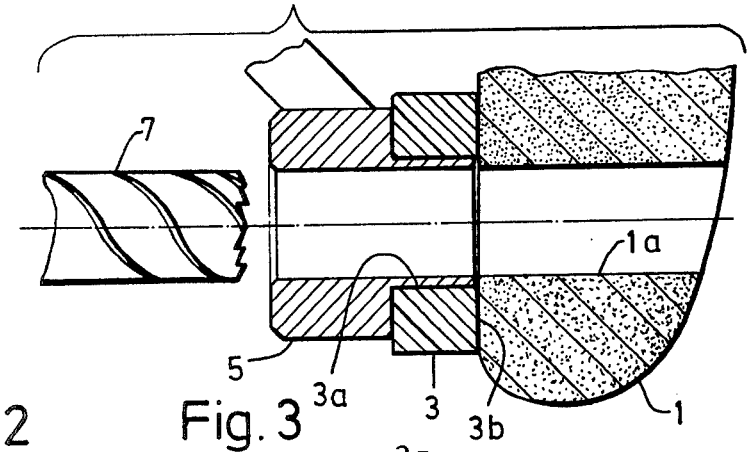
Fig. 1
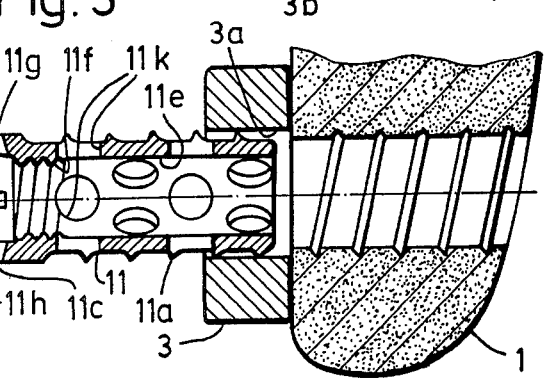
Fig. 2   Fig. 3
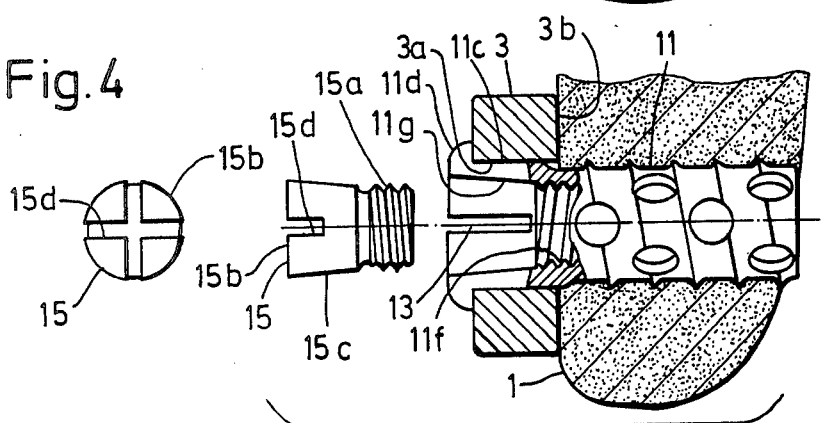
Fig. 4
Fig. 5

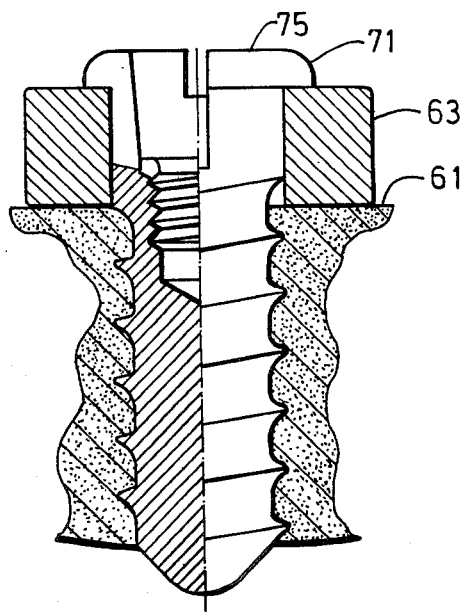
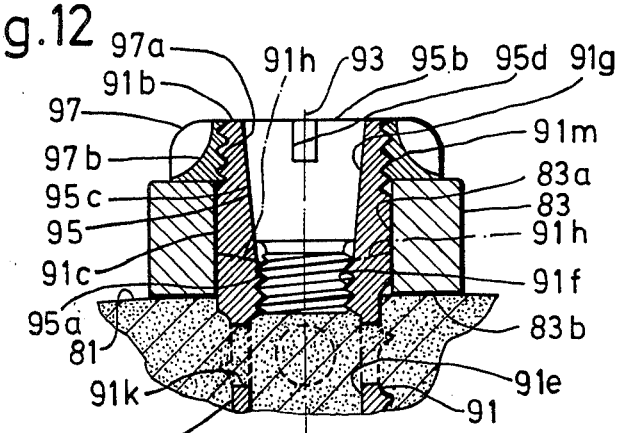
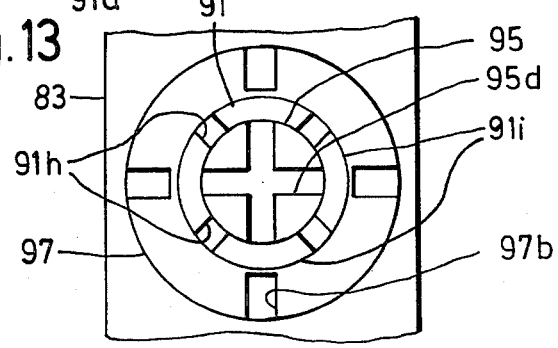

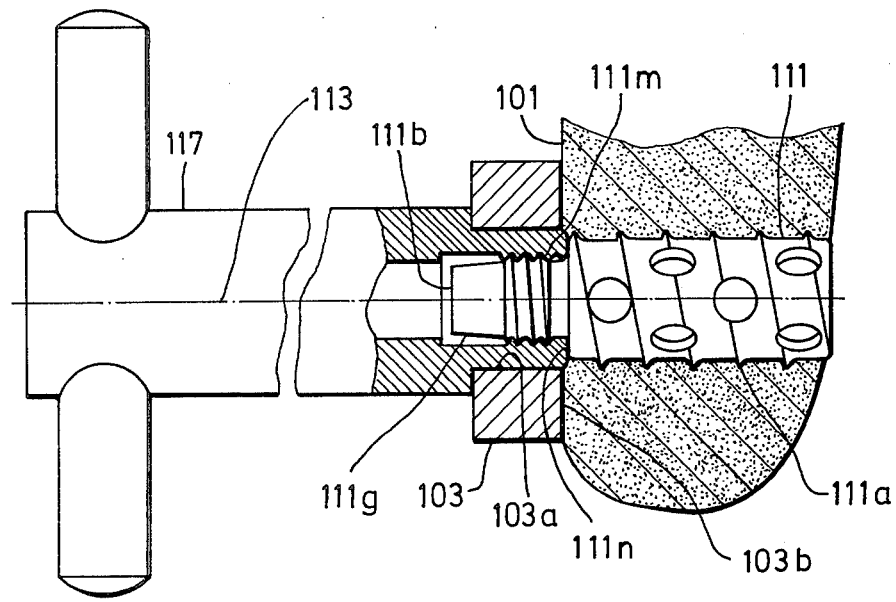
Fig. 14
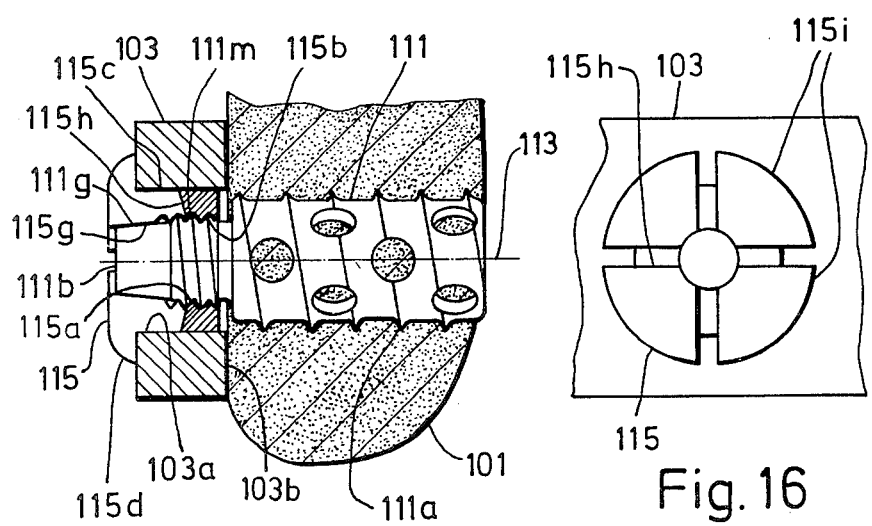
Fig. 15
Fig. 16

DEVICE COMPRISING AN IMPLANT AND SCREWS FOR FASTENING SAID IMPLANT TO A BONE, AND A DEVICE FOR CONNECTING TWO SEPARATED PIECES OF BONE

BACKGROUND OF THE INVENTION

1. Field of the Invention

The invention refers to a device comprising an implant with at least two clearance holes for screws, in particular a plate with holes, the device also comprising screws for fastening said implant to a bone and having a threaded portion to be screwed into the bone, and retaining means comprising a collar protruding in a generally radial direction and intended for retaining the implant at its side facing away from the bone.

The invention also refers to a device for connecting two separated pieces of bone at the place of their separation, comprising a plate with holes, furthermore screws for fastening the plate to the bone pieces and a flexible areal element to be disposed at the place of separation.

2. Description of the Prior Art

Devices comprising plates fastened by means of screws to broken bone pieces for the purpose of immobilizing these bone pieces have long been known in the field of bone surgery. Attention is called in this connection to U.S. Pat. No. 3,552,389. The Swiss Pat. No. 566 767 also discloses plates, which may be used in particular in jaw surgery. The screws of the known device comprise threaded portions of solid cross-section and heads with hemispherical bearing surfaces. The plates are provided with slots serving as clearance holes. Some of the slots may be provided with countersunk portions adapted to admit the screw heads and designed in such a manner, that the plate is displaces in a particular direction whenever the screw in question is screwed in place.

If, for example, in the course of a surgical operation two pieces of bone of the lower jaw must be connected with one another, the plate is properly formed and then fixedly fastened to the bone pieces, so that it makes contact with the two pieces under pressure. Experience has shown, however, that in many cases a reabsorption of the bone took place at the contact surface, a few weeks after the plate had been fastened. This happened in particular if time variable loads acting on the bone pieces, as tend to occur in the process of chewing, were large enough to cause sections of the plate to perform micromovements i.e. small movements relative to the bone pieces, in spite of the static compression force generated by the fastening process. Such reabsorption may cause open gaps to form between the plate and the bone pieces. The plate may then move back and forth between the screw head and the bone pieces in the longitudinal direction of the axis of the screw. Under certain circumstances this may cause the threaded portions of the screws screwed into the bone pieces to become loose too. The connection between the plate and the bone parts continues to get more and more loose, so that the plate stops fulfilling its function of fastening the bone pieces to one another.

Jaw tumors make it sometimes necessary to remove one piece of the jaw bone. In such a case too, the remaining bone pieces separated from one another by an open space are connected by way of a plate fastened by means of a screw connection. A sleeve possessing a certain stability of shape is then made of a plastically deformable wire lattice and placed over the two ends of the bone pieces facing one another. The space between the bone pieces bounded by the sleeve allows the insertion of bone material from other bones of the patient, so that the two bone pieces grow back together.

When surgically treating tumors of this kind, the bone pieces to be connected are not in contact with one another and are held together in the initial period after the operation by way of the screw-connected plate. In such cases it is of particular disadvantage to have the connection between the plate and the two pieces of bone become loose. On top of this, the sleeve surrounds the bone pieces in a loose way only.

An additional disadvantage of the known devices which shows itself in particular with plates comprising slot-shaped clearance holes, consists in that the micromovements taking place between the plate and the screws may cause frictional corrosion.

Mention is made here of the fact, that many different screw locking devices are known in the art. The Swiss Pat. No. 106 842, for example, discloses a screw locking device having a purpose not described in detail, but not intended for fastening implants. The screw icludes a slot with a wedge inserted into it. A wood screw is disclosed, among other things, provided with a conical screw head and a slot passing through one portion of the screw shaft. A metal wedge is driven into the slot and into the material of the screw-fastened portion surrounding the slot. This wedge is formed by a small plate essentially plane and provided at its forward edge with a wedge-shaped knife edge.

The Swiss Pat. No. 106 842 gives no indication to the effect that the screw locking devices disclosed therein are intended to be used for fastening implants. The screw locking device which comprises a wedge protruding sideways beyond the screw, as disclosed in Swiss Pat. No. 106 842, would in fact be unsuited for fastening an implant, because the wedge would have to be driven into the bone plate and possibly into the bone too. However, the wedge could only be driven into the bone plate, made for example of steel, if the plate had been initially provided with slots for receiving the wedge. However, slots of this kind would cause considerable weakening of the plate and, in addition, it would allow applying the wedge in certain definite positions of rotation of the screw only.

The Swiss Pat. No. 569 202 too, discloses a screw looking device comprising a screw with a head and a threaded portion, the latter being provided with slots at its end. The screw possesses a longitudinal opening with a conical portion located in the region of the slots and a threaded portion extending in continuation of the conical portion. An expander having a conical head a thread and a thinner shaft is screwed into the longitudinal opening. The Swiss Pat. No. 567 202 too, fails to give any indication relative to the possibility of using the screw locking device disclosed therein for surgical purposes. Since the device according to Swiss Pat. No. 569 202 is subject to expansion at the free end of the threaded portion of the screw, this device too, would offer no improvement in the connection between the screw and the bone plate.

The French Patent disclosure publication No. 2 193 161 refers to the riveting or the screw-fastening of sheet metal plates. A bushing provided with a conical inner surface is first inserted in each of the bores of the plates to be connected with one another. In one illustrated embodiment, a screw having a conical neck is then inserted in a manner to produce locking, subsequent to tightening the screw. Mention is made in this connection of the fact, that the bushing could be provided with a slot extending over its entire length. The French Offenlegungsschrift No. 2 193 161 this refers to the screw-fastening of sheet metal plates and does not contain anything that would indicate that the connection disclosed therein could be adapted to the fastening of bone plates.

SUMMARY OF THE INVENTION

Thus, the primary object of the invention is to create a device comprising a plate as an implant and screws, said implant to remain stably and rigidly connected to the bone pieces or the bone, respectively, even if reabsorption of bone material takes place.

The foregoing and other objects are attained in accordance with one aspect of the present invention by having each screw comprise at its end carrying the retaining means a clamping part known in the art and provided with slots and insertable into a clearance hole, and an expander, the said two parts being displaceable in known fashion in relation to one another in the longitudinal direction of the screw axis by way threads screwed into one another, and being provided with surfaces in contact with one another and coaxial with the screw axis and converging in the longitudinal direction of said screw axis, in such a way, that by displacing the expander, the clamping part may be made to expand and to become fixedly clamped within the clearance hole.

Advantageous embodiments of this device may include one or more of the following features:

The diameter of each of the converging surfaces of the two parts preferably decreases toward the end of the screw that faces away from the retaining means. The clamping part, when inserted into its clearance hole, has its slots extend from the collar end, through only one portion of the clearance hole.

The expander is preferably made of one piece with the screw, whereas the clamping part consists of a separate sleeve, or of a section of a separate sleeve. The part forming the collar may be loosenably screwed into the threaded portion of the screw intended to be screwed into the bone.

The converging surfaces preferably consist of conical surfaces. The slots of the clamping part preferably extend to the end surface of the clamping part which faces away from the threaded portion of the screw. Each screw preferably comprises a longitudinal opening open at least at the end of the threaded portion of the screw, each threaded portion also comprising holes opening into the longitudinal opening.

According to another aspect of the invention, the device for separating two separated pieces of bone includes a fastening element comprising a bolt and a collar, said areal element comprising a hole, through which the bolt may be passed through, but not the collar, the bolt being insertable into a hole of said plate and being loosenably fastenable to said plate.

Advantageous embodiments of this device may include one or more of the following features:

The fastening element may comprise a clamping part subdivided into tongues by means of slots, and an expander axially displaceable in relation to the clamping part, the said two parts including surfaces in contact with one another and converging in the longitudinal direction of the axis of the bolt, in such a way, that by displacing the expander, the clamping part may be made to expand and become fixedly clamped in relation to the hole in the plate. The converging surfaces are preferably conical surfaces.

The clamping part may be formed to advantage by a portion of said bolt, the bolt possessing a longitudinal opening, in which the expander is inserted.

This longitudinal opening preferably extends through the entire bolt, the expander being formed by a portion of an insert provided with a thread at its end facing away from the expander, a holding part being also provided, which may be screwed into said thread in order to pull the expander against the holding part and hold the areal element.

The fastening element preferably comprises a threaded part provided with an external thread and meant to be screwed into the bone. The areal element may, to advantage, be built in the form of a lattice.

BRIEF DESCRIPTION OF THE DRAWINGS

Various objects, features and attendant advantages of the present invention will be more fully appreciated as the same becomes better understood from the following detailed description of the present invention when considered with the accompanying drawings, in which FIG. 1 shows a sectional view of a portion of a lower jaw, a plate to be fastened thereto and a boring tool, FIG. 2 shows a top view of a head of a screw, FIG. 3 shows a sectional view of part of the lower jaw of FIG. 1, the plate, and the screw, FIG. 4 shows a top view of an insert with an expander, FIG. 5 shows a sectional view of a lower jaw, a plate connected therewith, and the insert to be screwed in, FIG. 11 shows a sectional view corresponding to FIG. 6 of a plate fastened to a lower jaw, the cross-section of the screw being solid, FIG. 12 shows a sectional view corresponding to FIG. 6, but comprising a variant of the screw in which the collar protruding at the head end of the screw may be removed, FIG. 13 shows a top view of the components shown in FIG. 12 without the bone, FIG. 14 shows a sectional view of a portion of a lower jaw and a plate fastened thereto by means of a different variant of a screw, and a tool used in the fastening process, FIG. 15 shows a sectional view corresponding to FIG. 14, but comprising a sleeve screwed onto the screw, FIG. 16 shows a top view of the components shown in FIG. 15 without the bone.

DETAILED DESCRIPTION OF THE PREFERRED EMBODIMENTS

Figure 6:
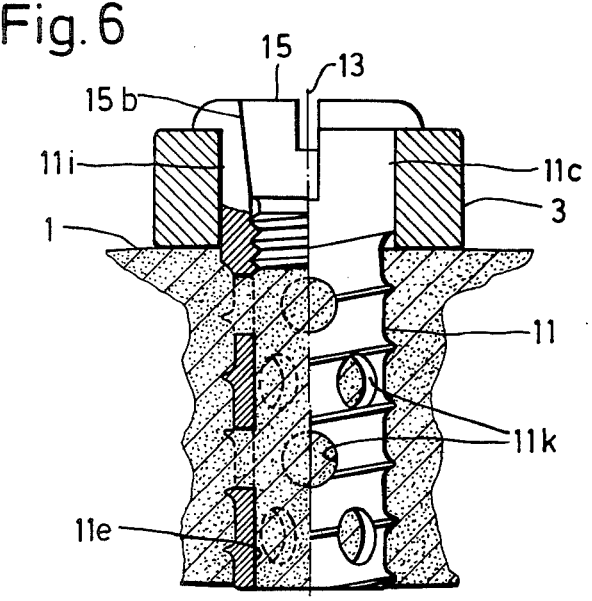
FIG. 6 shows a sectional view of the lower jaw and the plate connected therewith, after the bone material has grown together with the screw.

FIG. 1 shows a piece 1 of a lower jaw, or more accurately, of a lower jaw bone, which is to be connected by means of a device to another piece of the lower jaw. The device comprises an implant, in particular an elongated metallic plate 3 having at least two clearance holes 3a for screws distributed over its length. In the course of a surgical operation the plate 3 is bent to fit the shape of the bone and positioned as shown, so that its contact surface 3b bears against the bone piece 1. A hole 1a is bored subsequently into the bone piece 1, using a centering bushing 5 insertable into the clearance hole 3a and a cutting tool 7 only partially shown, which may be either a drill or a hollow milling cutter. An internal thread is subsequently cut in the hole 1a, preferably with a threading tool.

Metallic screws 11 are provided for fixedly mounting the plate 3, one of the screws being shown in each of the FIGS. 2 and 3. The screw 11 comprises a threaded portion 11a provided with an external thread. The screw 11 also comprises a head 11b. The head 11b includes a clamping part 11c made in one piece with the threaded portion 11a and having an essentially cylindrical outer surface, and a collar radially protruding beyond said outer surface. The diameter of the cylindrical outer surface of the clamping part 11c is approximately as large as the inner diameter of the clearance hole 3a, so that the clamping part 11c may be inserted to fit into the clearance hole 3a. The screw 11 is provided with a throughgoing longitudinal opening 11e which consists, within the major part of the threaded portion 11a, of a hole running coaxially with the screw axis 13. The longitudinal opening is provided with an internal thread 11f in the transition zone between the threaded portion 11a and the clamping part 11c. An internal conical surface 11g extends to the head end of the internal thread 11f. The diameter of the conical surface 11g gradually decreases from the head end face toward the tail end of the screw. The angle enclosed between the screw axis 13 and the conical surface 11g is less than 10°, for example 5°. The head is subdivided into four tongues 11i by four slots 11h running parallel to the screw axis 13 and extending in axial direction into the collar 11d and the major part of the cylindrical clamping part 11c. Disregarding the collar 11b, the radial cross-sectional dimensions of these tongues 11i are considerably smaller than the cross-sectional dimensions measured along the periphery of the screw. Therefore, the tongues 11i may be made to expand with relative ease away from the screw axis 13 by elastic deformation, but they remain relatively rigid in regards to any twisting around the screw axis 13. The screw 11 is provided on its threaded portion 11a with holes 11k distributed over its outer surface and opening into the longitudinal opening 11e.

Associated with each screw 11 is a screw-shaped insert 15 comprising a threaded portion 15a and an expander 15b. The threaded portion 15a may be screwed into the internal thread 11f. The expander 15b is bounded at its periphery by a conical surface 15c, the diameter of which decreases from the head toward the threaded part 15a. The angle enclosed by this conical surface 15c with the axis of the expander is the same as the angle enclosed by the conical surface 11 with the axis 13 of the screw. The expander 15b is provided with slots 15d cut into its face and made to cross each other at right angles.

The plate 3 is fastened to the bone by means of the screws 11, as shown in FIG. 5, a tool which engages their slots 11h being used for mounting the screws in place. As mentioned before, the bore 1a is threaded by means of a separate thread cutting tool before the screws are mounted in place. However, the screws themselves may be provided with tapping threads. In the mounted position of the screw 11 the collar 11d abuts against the surface of the plate which faces away from the bearing surface 3b of the plate 3. During the mounting process the plate is preferably fastened with one screw each to the two bone pieces. The appropriate holes are subsequently drilled in succession into the bone pieces for the other screws, which then are screwed in place to fixedly mount the plate.

An insert 15 is then mounted into each screw 11 by means of a tool, as shown in FIG. 6. This insert is screwed in longitudinal direction of the screw axis 13 to such a depth, that its expander 15b forces the tongue 11i apart, to lock the clamping part 11c of the screw 11 relative to the plate 3.

After the screws 11 have been in place within the bone pieces for a certain length of time, the bone material will have grown into the longitudinal openings 11e of the screws as well as into the holes 11k, as shown in FIG. 6. This makes the screws become very stably anchored within the bone.

Figure 7:
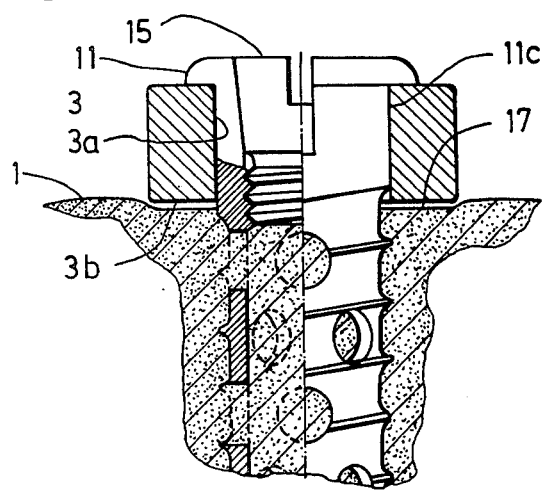
FIG. 7 shows a sectional view corresponding to FIG. 6, but referring to a case, in which a reabsorption of bone material has taken place in the region of the contact surface of the plate.

It will now be assumed, that a reabsorption of bone material has taken place in the region of the bearing surface 3b. This may occur for example, if time variable forces caused by external loads act on the bone or the bone pieces, as the case may be, and are sufficiently large to overcome the static compression force generated by fastening the plate 3. In such a case, the plate and the bone pieces begin to perform micromovements, i.e. small movements relative to one another. An open gap may then form, as a result of this reabsorption, between the bearing surface 3b of the plate 3 and the bone. A gap of this kind surrounding a screw 11 is illustrated in FIG. 7 and is indicated by the reference numeral 17 and shown, for the sake of clarity, as having its thickness largely exagerated. Should such a gap 17 indeed arise, the plate 3, which had been locked relative to the screw 11 by expanding the clamping part 11c, would stay connected with the screw in a manner rigid and axially non-displaceable. At the same time, the screw is prevented from becoming loose under the action of vibrations or other external forces. The bone material grown into the longitudinal opening 11 and the holes 11k contributes to preventing the screw 11 from becoming loose.

The device comprising the plate 3, the screws 11, and the inserts 15 mounted into the screws 11, fulfill the function of stably connecting bone pieces separated following a fracture or by other reasons, until they have grown back into a single bone again. By locking the screws relative to the plate and by the improvement in stability resulting therefrom is guaranteed, as mentioned before, that the connection between the plate and the screws is safe from loosening, even if reabsorption of bone takes place. Moreover, this improvement in stability acts inhibitingly on the formation and the development of bone reabsorption.

The previously described sequence of the surgical operation provided for the screws 11 to first be screwed tight and the inserts to be next inserted into the screws 11. As an alternative, the inserts could be loosely inserted into the screws and held in place without expanding the clamping parts of the latter. After mounting the screws inside the bone pieces the inserts must be screwed-in further and displaced in the axial direction only to the depth required for the expansion of the clamping part.

As soon as the bone pieces have grown together the plate 3 may be removed. For this purpose, the plate is first laid open and the inserts 15 are loosened. In dependence on how much bone has grown around the screws the surgeon may now loosen the screws 11, or he may press the tongues 11i together, by means of a pair of pliers, and bend the plate 3 or pull it away over the heads 11. In the latter case, the heads of the screws protruding from the jaw bone may be milled off after removing the plate.

Figure 8:
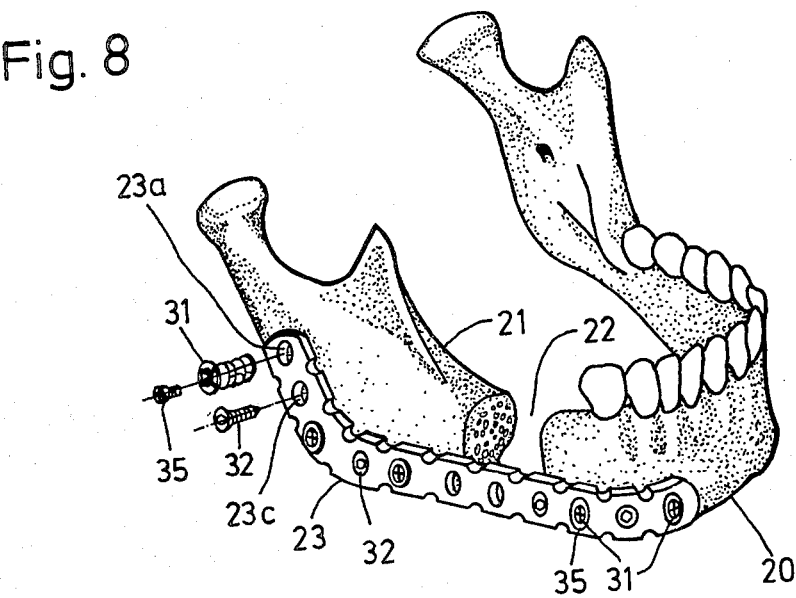
FIG. 8 shows an axonometric view showing two pieces of a lower jaw connected by means of a plate.

FIG. 8 shows a lower jaw, one piece of which had to be removed because of a tumor. The jaw becomes thus divided into two bone pieces 20 and 21 separated from one another by an empty space. The two bone pieces 20 and 21 are connected with each other by means of the plate 23. This plate 23 comprises the clearance holes 23a, which correspond to the clearance holes 3a of plate 3, and the countersink clearance holes 23c in an alternating arrangement. The plate 23 is fastened to the bone pieces 20 and 21 by means of the screws 31, simlar to the screws 11, and the countersink head screws 32, whereby the screws 31 are inserted through the holes 23a and the screws 32 through the holes 23c. The clamping parts of the screws 31 are locked within the plate 23 by way of the inserts 35 similar to the inserts 15. The countersink head screws 32, on the other hand, are not locked. It should be noted, however, that the fastening of the plate could just as well be accomplished by lockable screws 31 alone.

Figure 9:
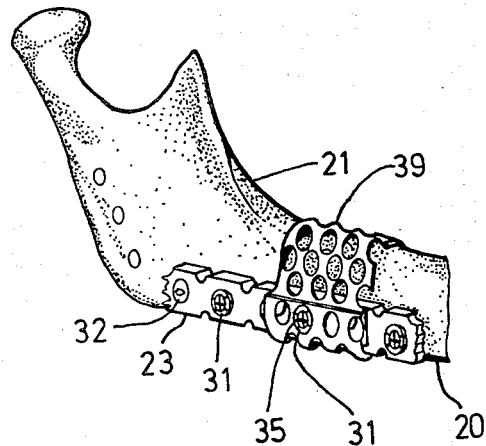
FIG. 9 shows a cutout portion of FIG. 8 also comprising a sleeve surrounding the ends of the bone pieces facing each other.

After the plate has been fastened to the bone pieces 20 and 21 a sleeve 39 shown in FIG. 9 is applied in the manner previously described in connection with the plate 3. The sleeve consists of an areal, latticed, flexible element made of a metal strip and provided with round holes distributed over its surface in the configuration of a sieve. The sleeve 39 surrounds the space 22 and is supported by the two ends of the bone pieces 20 and 21 facing one another. The two ends of the strip constituting the sleeve are made to overlap and bear against the outside of the plate 23. The sleeve 39 is fastened to the plate 23 by means of one of the screws 31 made to pass through aligned holes of the overlapping sleeve edges and through a clearance hole 23a, and is locked tight by means of the insert 35. The length of this screw 31 is chosen to have its threaded portion pass through the open space 22 and through one hole of the sleeve located on the side thereof facing away from the plate. The screw 31 thus holds the sleeve 39 on that side of the open space 22 too, which faces away from the plate 23.

At least one of the screws 31 with its insert 35 may thus be used as a fastening element, for loosenably fastening the sleeve 39 on the plate 23. Since the screw thread fulfills no particular function in this fastening process, the screw could be replaced by a fastening element lockable within the hole 23a and comprising only a smooth pin instead of the threaded portion.

Bone material removed from another bone of the patient may be introduced into the space 22 surrounded by the sleeve 39, when mounting the sleeve. After a certain amount of elapsed time the bone material will have grown enough to make the two pieces of bone 20 and 21 get united into a single bone. The plates 23 and the sleeve 39 may then be removed.

Figure 10:
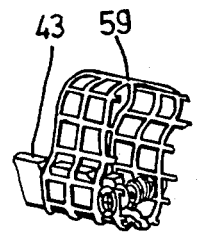
FIG. 10 shows an axonometric view of a piece of a plate and a variant of a sleeve.

FIG. 10 shows a portion of a plate 43 with a latticed sleeve 59 fastened to it, comprising square holes. A screw similar to the screw 31 serves for fastening the sleeve and is locked tight relative to the plate.

FIG. 11 shows a bone piece 61, a plate 63, a screw 71 and an insert 75. The screw 71 differs from the screw 11 by the fact, that its threaded portion has a solid cross-section and no radially extending holes. For the rest, the plate 63, the screw 71 and the insert 75 may be analogous to the plate 3, the screw 11 and the insert 15.

FIGS. 12 and 13 show an embodiment of a device comprising a plate 83 with circular holes 83a bearing with its surface 83b against a first bone piece 81 and against a second bone piece. A screw 91 is screwed into the bone piece at each clearance hole 83a by way of the threaded portion 91a. The screw 91 comprises a head portion 91b protruding from the bone and formed into a clamping part 91c in the region of the clearance hole 83a. The screw 91 is provided with a throughgoing longitudinal opening 91e disposed coaxially with the screw axis 93. The longitudinal opening 91e is provided with an internal thread 91f located at the transition zone between the threaded portion 91a and the head portion 91b. An internal conical surface 91g is provided in extension of the thread 91f. The clamping part 91c is subdivided into four tongues 91i, by means of slots 91h running parallel to the axis 93 and cut into the face of the head portion 91b of the clamping part 91c. The threaded portion 91a is provided with holes 91k opening into the longitudinal opening 91e. Whereas the section of the clamping part 91c disposed within the clearance hole 83a is bounded in the main by a smooth cylindrical outer surface, the upper end of the head portion 91b which protrudes beyond the clearance hole 83a is provided with an external thread 91m.

The insert 95 comprises a threaded portion 95a screwed into the internal thread 91f and an expander 95b outwardly bounded by a conical surface 95c, the diameter of which decreases toward the threaded portion 95a. The expander 95b has two slots 95d cut into its face and crossing one another. A collar 97 shaped like a ring and serving as a nut comprises an internal thread 95a screwed onto the outer thread 91m. The collar 97 is provided with four slots 97b engageable by means of a tool specially suited for the purpose.

When fastening the plate 83 to the bone pieces by means of the screws 91, the collar bears against the plate surface disposed opposite the bearing surface 83b and thus holds the plate 83 tight against the bone pieces. Also, the clamping part is expanded by means of the expander 95 and locked tight within the plate 83. The threads 91m and 97a serving for fastening the collar 97 are designed to not interfere with the expansion of the tongues 91i within the clearance hole 83a.

The screw 91 thus differs from the screw 11 by the fact, that the collar 97 which protrudes radially in relation to the screw axis 93 is not made in one piece with the remainder of the screw 91, but is loosenably connected with it. This makes the plate 83 removable from the bone pieces and the screws 91, by unscrewing the collars 97 from the screws 91 and partially unscrewing the inserts. This mode of fastening the plate is particularly useful in cases in which the plate must be removed from time to time for treating a tumor with radiation.

Another embodiment of the device, in which a plate 103 comprising cylindrical clearance holes 103a and a bearing surface 103b may be loosened with relative ease from a bone or a bone piece 101 and from the screws 111 screwed into the latter, is shown in FIGS. 14, 15 and 16. The screw 111 has a threaded portion 111a provided with an external thread and a neck of smaller diameter. A radial shoulder surface 111n surrounding the neck is provided at the transition between the threaded portion 111a and the neck. The axis of the screw is identified by the reference numeral 113. The portion of the neck adjacent to the threaded portion 111a is also provided with an external thread 111m, running in the same sense as the thread of the threaded portion 111a. An expander 111b provided adjacent to the external thread 111m is outwardly bounded by a conical surface 111g. The diameter of the latter surface decreases from the threaded portion 111a toward the free end of the expander 111b. The threaded portion 111a comprises a longitudinal opening starting at the end thereof which faces away from the expander 111b, and holes radially opening into the longitudinal opening.

If a plate 103 is to be fastened to bone pieces, the latter are provided with a threaded hole for each screw 111. The tool 117 shown in FIG. 14 is used for mounting the screws 111. This tool 117 is provided at its forward end with a threaded hole adapted to receive the neck of the screw 111, which may be screwed in to a depth at which its shoulder surface 111n abuts against the forward end surface of the tool. This forward portion of the tool may be inserted with little play into the clearance hole 103a. The tool 117 also includes a radial shoulder surface which, in the process of screwing the screw into a bone piece, will come to bear against the plate 103, thus determining the depth to which the screw 111 may be advanced.

As soon as the screw 111 is mounted in the manner shown in FIG. 14, the tool may be disengaged from the screw. The sleeve 115 shown in FIGS. 15 and 16 is then screwed onto the neck of the screw 111. This sleeve 115 comprises a throughgoing longitudinal opening 115a provided with an internal thread 115b at its end turned toward the bone piece. An internal conical surface 115 having a cone angle corresponding to that of the conical surface 111g is provided in continuation of the internal thread 115b. The sleeve 115 also comprises a clamping part 115c provided with an essentially cylindrical outer surface having a diameter approximately equal to the internal diameter of the clearance hole 103a. At its side facing away from the plate 103 the sleeve 115 is provided with a collar 115d protruding radially outwardly and being made in one piece with the sleeve. The clamping part 115c is somewhat shorter in the axial direction than the clearance hole 103a, so that it stays in its entirety within the hole 103a. The slots 115h subdivide the collar 115d and a portion of the clamping part 115c into four tongues 115i.

Screwing the sleeve 115 onto the neck of the screw 111, as shown in FIG. 15, by means of a tool engaging the slots 115h, will make the collar 115d bear against the plate surface disposed opposite the bearing surface 103b, and hold the plate 103 fastened to the bone piece 101. At the same time, the tongues 115i will be forced apart by the expander 111b, locking the clamping part 115 within the plate 103.

For removing the plate 103, e.g. for a temporary radiation treatment, the sleeves 115 shall be unscrewed from the neck portions of the screws 111. The plate 103 may then be readily removed.

In order to have the sleeve 115 and its collar bear against the plate with a certain amount of pressure and to have it properly expand in its position, the screw must have been screwed-in initially to the proper depth, as was explained with reference to FIG. 14. As an additional requirement, the screw 111 is not to turn or change its position during the disengagement of the tool 117 and the fastening of the sleeve 115. These requirements may be readily fulfilled by properly designing the various threads of the screw 111, the tool 117, the sleeve 115 and the threaded hole drilled into the bone piece.

As an alternative, the screw 111 could be provided with other means, for example with grooves surrounding its neck, which the tool could engage with without being subjected to rotation. In such a case, the tool could be applied to the screw neck by subjecting it to a motion parallel to the screw axis. This would eliminate the need of screwing the tool onto the neck and then unscrewing it again.

Figure 17:
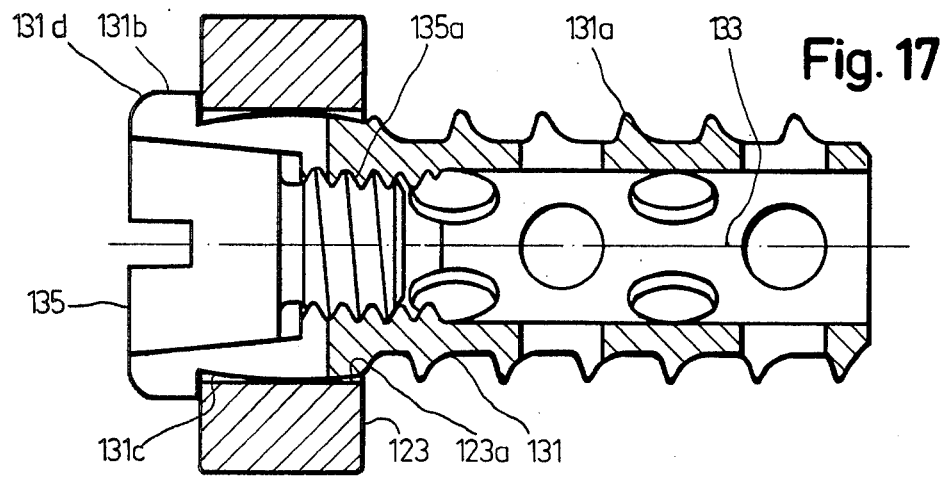
FIG. 17 shows a sectional view of a plate and a variant of the screw, the outer surface of the clamping part being shaped convex.

FIG. 17 shows a plate 123 with circular clearance holes 123a. A screw 131 comprises a threaded part 131a and a head 131. The head 131 includes a clamping part 131c and a collar 131d. An insert 135 comprising a threaded portion 135a and an expander 135b is inserted into the screw 131. The outer surface of the clamping part 131c is somewhat convex and forms a spherical zone, for example, comprising an equator and being symmetrical with respect thereto. Apart from this convexity of the outer surface of the clamping part 131c, the embodiment shown in FIG. 17 is essentially equivalent to the device shown in FIGS. 1 to 6. The convex design of the clamping part 131c enables the surgeon to tilt the screw axis 133 to a certain extent in relation to the axis of the hole 123a. This may be useful in a case, in which a hole drilled into the bone, by accident or by intent, has its axis not perpendicular to the plate, i.e. not parallel to the axes of the other holes drilled into the bone.

Figure 18:
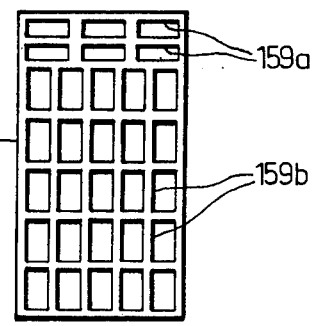
FIG. 18 shows a top view of a latticed element.

FIG. 18 shows an areal, flexible, latticed element 159 serving a purpose similar to that of the sleeves 39 and 59. This element 159 could have had the plane configuration shown in FIG. 18 before its use. The element 159 is rectangular in shape and comprises for example two rows of holes 159a extending along one of its margins. The holes 159a are shaped like rectangular slots and have their larger sides disposed parallel to the respective margin. The remaining portion of the element 159 comprises holes 159b uniformly distributed in several rows. These holes too, have the shape of rectangular slots, their longer sides extending, however, at right angles to the longer sides of the holes 159a. The holes 159b are also wider than the holes 159a.

Figure 19:
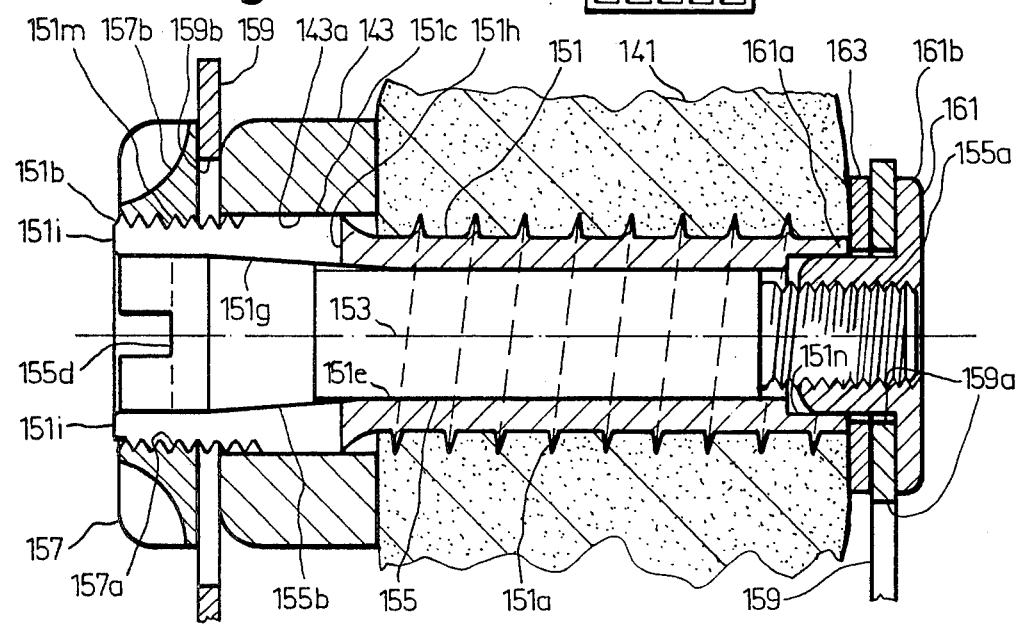
FIG. 19 shows a sectional view of a bone, a plate fastened thereto, a fastening element, and a latticed element fastened by means of said fastening element.

FIG. 19 shows a section through a lower jaw bone 141. In a manner similar to the bone shown in FIG. 8, the bone 141 is broken into two pieces separated by an open space near the sectional plane of the FIG. 19. These two pieces are connected by means of the plate 143 comprising the clearance holes 143a. The plate 143 may be fastened to the two pieces of the bone 141 in a manner similar to the plate 23. Fastening elements serving, on one side, for loosenably fastening the plate 143, on the other side, for loosenably fastening the element 159 bent into a C-shaped or U-shaped channel are provided nearest to the said open space, but still within the range of one of the clearance holes 143a located near the end of one of the bone pieces. These fastening elements, one of which is also shown in FIG. 19, consist each of a screw 151 comprising a threaded portion 151a screwed into a bone piece, and a head portion 151b provided with an expandable clamping part 151c in the region of the clearance hole 143a. The clamping part 151c is subdivided into the tongues 151i by means of four slots 151h cut into the face of the screw 151. The screw 151 is provided with a longitudinal throughgoing opening 151e coaxial with the screw angle 153 and comprising a cylindrical central section. The screw 151 is also provided, in the region of the clamping part 151c, with a section diverging toward the end of the screw and bounded by an internal conical surface 151g, and continued by a short cylindrical section. The longitudinal opening 151e comprises an enlargement 151n at the other end of the screw 151. The head portion 151b includes a section protruding from the clearance hole 143a of the plate 143 and comprising an external thread 151m surrounded by a ring 157 provided with an internal thread 157a and the slots 157b. The clamping part 151c and the ring 157 are similar to the corresponding parts of the device shown in FIGS. 12 and 13. The head portion 151b penetrates through a hole 159b of the element 159, between the plate 143 and the ring 157.

The hollow threaded portion 151a may comprise a solid peripheral wall, as shown in FIG. 3, or a peripheral wall penetrated by holes, similar to those of the screw 11.

An insert 155 made in one piece in the shape of a bolt is inserted into the opening 151e and comprises a central portion positioned with little play in the central portion of the opening 151e. A thinner threaded portion 155a comprising an external thread extends from one end of said central portion, and an expander 155b from the other end thereof, said expander 155b including a conically diverging section followed by a short cylindrical section at the larger end of the conical section. The cylindrical section is provided with slots 155d crossing one another at right angles.

A holding element in the shape of a nut 161 includes an internally threaded bushing 161a and a collar 161b protruding radially away from the bushing. The bushing 161a penetrates through a hole 159a of the element 159, it enters the enlargement 151n and is screwed onto the threaded portion 155a of the insert 155. An additional ring 163 is positioned between the element 159 and the face of the screw 151 turned toward the element 159.

The widths of the slot-shaped holes 159a, 159b are chosen to be only somewhat larger than the corresponding outer dimensions of the parts entering them, such as the bushing 161 and the head portion 151b. If the insert 155 and the nut 161 are only loosely connected with one another, the end of the element 159 adjacent to the nut 161 may, therefore, be displaced, within the limits set by the length of the slot-shaped holes 159a, only at right angles to the sectional plane of FIG. 19. The end of the lement 159 adjacent to the head portion 151b, on the other hand, may be displaced only at right angles to the screw axis 153 in the sectional plane 19.

During a surgical operation involving the jaw bone 141 the plate 143 is first fastened by means of a few screws to the bone pieces. One screw 151 each is then inserted into the clearance holes 143a nearest the open space separating the bone pieces but located on different sides of said open space, to such a depth, that the ends of their threaded portions 151a be approximately flush with the inner side of the appropriate bone piece. An insert 155 is subsequently placed into the longitudinal opening 151e. The element 159 is then properly bent, so that it may be passed below the underside of the bone, and then loosely connected with the insert 155 by means of the nuts 161 and the rings 163, at first at the holes 159a, for example. Then, at its other end too, the element 159 is first loosely connected to the screws 151 by means of the rings 157. The surgeon may now adjust the element 159 and bend it into its final shape, and then tightly fasten the insert 155 and the ring 157. While fastening the insert 155, the expander 155b forces the clamping part 151c apart, so that the latter becomes locked relative to the plate 143. The element 159 then forms a channel open at the top, through which bone material may be introduced, which, in the course of time, will grow together with the bone pieces of the bone 141.

The enlargement 151n and the bushing 161a may be cylindrical in design and dimensioned to make them properly fit into one another. However, the enlargement 151n and the bushing 161a could be provided with square perimeters or at least with two plane surfaces parallel to the axis 153. In this way, the bushing projecting into the enlargement 151n becomes connected with the screw 151 non-rotatably, which facilitates the tightening of the insert 155.

The length dimensions of the screws 151 should approximately correspond to the thickness dimensions of the bone pieces. Inasmuch as the rings may be screwed to a greater or smaller depth, they allow a certain degree of adjustment to the thickness of the bone. It therefore suffices, to prepare a set of screws with length dimensions increasing in steps to enable the surgeon to select the proper screws during the operation.

If necessary, the surgeon may insert a screw into a clearance hole 143a located in the region of the open space between the two bones. In such a case the screw evidently cannot be screwed into the bone and must be fastened to the plate 143 exclusively by forcing the clamping part 151c apart. Since the threaded part 151a is not absolutely required for this application, the screws 151 may be replaced by fastening bolts having a smooth cylindrical surface in lieu of the threaded portion 151a.

The components of the devices described above may be made of various metals or alloys, or even of non-metallic materials.

A method, by which a plate serving as an implant may be used for immobilizing bone pieces has been described above with reference to various embodiments. Plates of this kind are generally removed after a certain amount of time, the screws, however, are sometimes left in the bone.

A prosthesis intended for a durable stay in the body may be fastened as an implant in a manner similar to that described above for the plate. If, for example, an artificial knuckle is to be mounted to a lower jaw, a prosthesis including an artificial knuckle and a plate-shaped component could be provided. This latter component could then be fastened to the remaining bone in the manner described above for the plate.

Furthermore, the width and/or height dimensions of the plates may be enlarged at the clearance holes to make the bending resistance moment approximately constant at least at the two clearance holes and between them, or even along the entire length of the plate. Attention is called in this connection to U.S. Pat. No. 4,219,015.

Obviously, numerous modifications and variations of the present invention are possible in the light of the above teachings. It is therefore to be understood that within the scope of the appended claims the invention may be practiced otherwise than as specifically described herein.

I claim:

1. A device for mounting an implant in a bone, said implant having at least two clearance holes, the device comprising screws extending through said holes for fastening the implant to a bone, each of said screws having a central axis and including a threaded portion to be screwed into the bone and one end facing away from the bone, said threaded portion of each of said screws having a longitudinal opening that opens in another screw end facing toward the bone and a plurality of lateral holes opening into said longitudinal opening; and retaining means on said one end of each of said screws, said retaining means including a collar provided on said one end and projecting substantially radially outwardly from said central axis and engaging the implant at its side facing away from the bone, a clamping part provided in said one end and having slots and insertable in the clearance hole of the implant, and an expander at least partially insertable in said clamping part so that said longitudinal opening of said threaded portion of each of said screws is at least in part free and the bone can grow into said longitudinal opening and through said lateral holes, said expander and said clamping part being displaceable in an axial direction relative to each other and being provided with surfaces in contact with one another, said surfaces converging in said axial direction, whereby by axially screwing said screws into the bone said collar of said one end of each screw presses the implant against the bone, and by displacing said expander in said axial direction said clamping part of said one end expands and becomes fixedly clamped within the clearance hole of the implant.

2. A device as claimed in claim 1, wherein the diameter of the converging surface decreases toward the end of the screw facing away from the retaining means.

3. A device as claimed in claim 1, wherein the expander is made in one piece with the screw, and the clamping part consists of a portion of a separate sleeve.

4. A device as claimed in claim 1, wherein the part forming the collar is separably screwed onto the threaded portion of the screw to be screwed into the bone.

5. A device as claimed in claim 1, wherein the converging surfaces are conical surfaces.

6. A device is claimed in claim 1, including means for displacing said clamping part relative to said expander.

7. A device as claimed in claim 1, wherein said clearance holes comprise a cylindrical portion and wherein the clamping of each of said clamping parts takes place in said cylindrical portion so that the clamping secures the screws against displacements in both directions along the screw axis relative to the implant.

8. A device as defined in claim 1, wherein the portion of said clamping part being clamped with the clearance hole has a cylindrical exterior surface.

9. A device as defined in claim 1, wherein said implant is a plate.

10. A device as claimed in claim 9, wherein said plate has at said clearance holes at least one cross-sectional dimension that is greater than the said dimension between the holes.

11. A device according to claim 1, wherein the clamping part and the expander comprise thread means engaging each other and allowing the axial displacement of the expander and the clamping part relative to each other.

12. A device for mounting an implant in a bone, said implant having at least two clearance holes, the device comprising screws extending through said holes for fastening the implant to a bone, each of said screws having a central axis and including an threaded portion to be screwed into the bone and an end facing away from the bone; and retaining means on said end of each of said screws, said retaining means including a collar projecting substantially radially outwardly from the central axis of each screw and engaging the implant on its side facing away from the bone, a clamping part provided in said end of each screw, said clamping part having slots and being insertable in the clearance hole of the implant, and an expander at least partially insertable in said clamping part, said expander and said clamping part being displaceable in an axial direction relative to each other and being provided with surfaces in contact with one another, said surfaces converging in said axial direction, whereby by screwing said screws into the bone, said collar at said end of each screw presses the implant against the bone, and by displacing said expander in said axial direction, said clamping part expands and becomes clamped within the clearance hole of the implant, each of said screws being expandable only in the region of said retaining means.

13. A device for connecting two separated pieces of bone comprising a plate having at least three clearance holes, screws for insertion in certain of said clearance holes for attaching said plate to each of said bone pieces and a flexible areal element to be positioned at the place of separation, each of said screws having a central axis and including a threaded portion to be screwed into the bone and one end facing away from the bone, said threaded portion of each of said screws having a longitudinal opening that opens in another screw end facing toward the bone and a plurality of lateral holes opening into said longitudinal opening; and retaining means on said one end of each of said screws, said retaining means including a collar provided on said end, projecting substantially radially outwardly from said central axis and engaging the plate on its side facing away from the bone, a clamping part provided in said one end and having slots and insertable in the clearance hole of the plate, and an expander at least partially insertable in said clamping part so that said longitudinal opening of said threaded portion of each of said screws is at least in part free and the bone can grow into said longitudinal opening and through said lateral holes, said expander and said clamping part being displaceable in an axial direction relative to each other and being provided with surfaces in contact with one another, said surfaces converging in said axial direction, whereby by axially screwing said screws into the bone said collar of said one end of each screw presses the plate against the bone and by displacing said expander in said axial direction said clamping part of said one end expands and becomes fixedly clamped with the clearance hole of the plate, said areal element comprising a hole sized to receive the threaded portion of one of said screws but being sized smaller than said collar.

14. A device as claimed in claim 13, wherein the said converging surfaces are conical surfaces.

15. A device as claimed in claim 13, wherein the areal element is made in the form of a lattice.

* * * * *